United States Patent

Okada et al.

[11] Patent Number: 4,621,144
[45] Date of Patent: Nov. 4, 1986

[54] 1-PHENYL-4-HYDROXYPYRAZOLE DERIVATIVES

[75] Inventors: Yoshiyuki Okada, Suita; Yasuo Sato, Kyoto, both of Japan

[73] Assignee: Takeda Chemical Industries, Ltd., Osaka, Japan

[21] Appl. No.: 627,728

[22] Filed: Jul. 3, 1984

Related U.S. Application Data

[60] Division of Ser. No. 511,296, Jul. 6, 1983, Pat. No. 4,474,775, which is a continuation of Ser. No. 304,258, Sep. 14, 1981, abandoned, which is a continuation of Ser. No. 136,460, Mar. 31, 1980, abandoned.

[30] Foreign Application Priority Data

Mar. 30, 1979 [JP] Japan ................................. 54-38957

[51] Int. Cl.$^4$ ............................................ C07D 231/18
[52] U.S. Cl. .................................... 548/358; 548/116
[58] Field of Search ......................... 548/358, 374, 116

[56] References Cited

U.S. PATENT DOCUMENTS

| | | | |
|---|---|---|---|
| 2,981,740 | 4/1961 | Henkel et al. | 548/358 |
| 4,163,052 | 7/1979 | Hofer et al. | 424/200 |
| 4,315,008 | 2/1982 | Maurer et al. | 424/200 |

FOREIGN PATENT DOCUMENTS

| | | | |
|---|---|---|---|
| 184580 | 2/1956 | Austria | 548/116 |
| 519436 | 12/1955 | Canada | 548/358 |
| 2639258 | 3/1978 | Fed. Rep. of Germany | |
| 2310353 | 12/1976 | France | |

OTHER PUBLICATIONS

Maurer et al, Chemical Abstracts, 87:201527x, 1977.
Okada et al., The Fifth International Congress of Pesticide Chemistry, Aug. 29–Sep. 4, 1982, Kyoto, Japan.
Chattaway et al., J. Chem. Soc., 1933, p. 475–479.

Primary Examiner—Richard A. Schwartz
Assistant Examiner—Kurt G. Briscoe
Attorney, Agent, or Firm—Wenderoth, Lind & Ponack

[57] ABSTRACT

A compound of the formula:

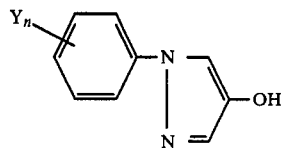

wherein Y is alkyl of 1 to 4 carbon atoms, alkoxy of 1 to 4 carbon atoms, alkylthio of 1 to 4 carbon atoms, a halogen atom, nitro or trifluoromethyl; and n is an integer of 1, 2 or 3; and when n is 2, $Y_n$ may be an alkylidenedioxy group; or a salt thereof. These compounds are useful in producing pyrazol-4-yl phosphates which posess insecticidal-acaricidal activity.

5 Claims, No Drawings

1-PHENYL-4-HYDROXYPYRAZOLE DERIVATIVES

This application is a division of Ser. No. 511,296, filed July 6, 1983, now U.S. Pat. No. 4,474,775, which is a continuation of Ser. No. 304,258, filed Sept. 14, 1981, now abandoned, which is a continuation of Ser. No. 136,460, filed Mar. 31, 1980, now abandoned.

The present invention relates to pyrazolyl phosphoric acid esters which are novel compounds, a method for the preparation thereof, and an insecticidal-acaricidal composition.

In more particular, the present invention relates to pyrazolyl phosphoric acid esters represented by the general formula (I):

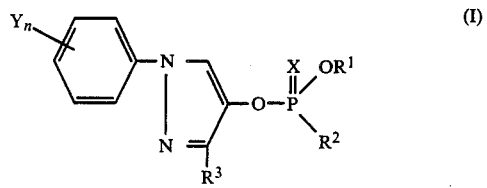

wherein $R^1$ represents a lower alkyl group; $R^2$ represents a lower alkoxy or a lower alkylthio group; $R^3$ is hydrogen or a lower alkoxycarbonyl group; X is oxygen or sulfur; Y is a lower alkyl, a lower alkoxy or a lower alkylthio group, a halogen atom, nitro or trifluoromethyl; and n is zero or an integer of 1, 2 or 3. The invention also provides a method for the preparation of these esters, and an insecticidal-acaricidal composition containing them as an effective ingredient.

The present inventors, with a specific view to the development of insecticides or acaricides which could be produced profitably on an industrial scale and could be safely applied without substantial toxicity to warm-blooded animals and fished, without presenting any substantial drug damage to plants, synthesized a large number of organic compounds and conducted considerable repeated investigation through biological and other tests. As a result, it has been found that the compounds according to the present invention as represented by the general formula (I) hereinbefore described exhibit an excellent insecticidal-acaricidal activity against plant damaging insects, mites parasitic on plants and unsanitary pests including ticks parasitic on warm-blooded animals, etc. and that they can be profitably produced on an industrial scale.

In the general formula (I), the lower alkyl group designated by $R^1$ means straight-chain or branched alkyls of 1 to 4 in carbon atom number, and examples thereof that may be utilized include methyl, ethyl, n-propyl, isopropyl, n-butyl, isobutyl, sec-butyl, etc.; the lower alkoxy group represented by $R^2$ means alkoxy groups of 1 to 4 in carbon atom number, being exemplified by methoxy, ethoxy, n-propoxy, isopropoxy, n-butoxy, isobutoxy, sec-butoxy, etc.; the lower alkylthio group represented by $R^2$, means alkylthio groups of 1 to 4 in carbon atom number, being exemplified by methylthio, ethylthio, n-propylthio, isopropylthio, n-butylthio, isobutylthio, sec-butylthio, etc.; the lower alkoxycarbonyl group designated by $R^3$ may for example be alkoxycarbonyl groups in which the alkoxy has 1 to 4 carbon atoms, such as methoxycarbonyl and ethoxycarbonyl; among the groups shown by Y, the lower alkyl, lower alkoxy and lower alkylthio groups have the same meanings as defined for $R^1$ and $R^2$, respectively, and examples of the lower alkyl group may include t-butyl in addition to those described hereinbefore; as examples of the halogen atoms there may be mentioned fluorine, chlorine, bromine and iodine atoms; n represents a number of substituents of Y, and when n is not less than 2, these substituents may be the same or different. Furthermore, in the event that the groups represented by Y are lower alkoxy groups with n equal to 2, within the scope of the present invention falls the case where two of the alkoxy groups combine to form an alkylidenedioxy group containing 1 to 3 carbon atoms such as methylenedioxy and isopropylidenedioxy groups.

A desirable class of compounds (I) comprises the compounds wherein $R^1$ represents a lower alkyl group, $R^2$ is a lower alkylthio group, $R^3$ is hydrogen, X is oxygen or sulfur atom, Y represents a halogen atom or trifluoromethyl, and n is an integer of 1, 2 or 3. A family of the particularly important compounds comprises the compounds of the general formuula (I) wherein $R^1$ means ethyl group, with $R^2$ representing n-propylthio group. In addition, important is a group of the compounds wherein $R^3$ means hydrogen.

The compounds according to the present invention have a strong insecticidal-miticidal activity against many insects and mites and, while they retain such excellent action, possess the characteristic feature of being relatively low in oral, acute toxicity. Those compounds having the combination of $R^1$ being ethyl and $R^2$ n-propylthio, which are the especially important compounds among the ones according to the present invention, exhibit excellent preventive and exterminating effect, particularly, against noxious insects such as Lepidoptera and mites or ticks, while being low in acute toxicity toward warm-blooded animals when orally ingested. This activity manifests itself not only when the compound of this invention is directly applied to pests, for example by spraying it on host plants, but also when the compound (I) absorbed by plants from the roots, leaves, stems or the like comes into contact with pests as, for example, the latter suck or gnaw the plant.

The compounds (I) according to the present invention may be produced by a method conventional per se, and, for example, by esterifying a compound of the general formula (II) as shown below or its salt:

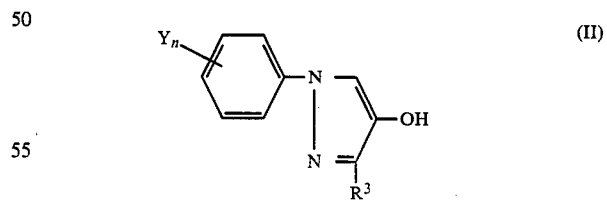

wherein $R^3$, Y and n are as defined hereinbefore, with a compound of the general formula (III):

wherein Hal is a halogen atom; $R^1$, $R^2$ and X are as defined hereinbefore. The esterification reaction is desirably conducted in the presence of an acid-binding agent.

Employed as the appropriate acid-binding agent are, especially, tertiary amines such as trialkylamine, pyridine and γ-collidine, or hydroxides, carbonates and bicarbonates of alkali and alkaline earth metals and alcoholates of alkali metals such as sodium carbonate, potassium carbonate, sodium hydrogencarbonate, sodium hydroxide, potassium hydroxide, sodium methylate and sodium ethylate. Among salts of 4-hydroxypyrazole compounds of the general formula (II), the corresponding alkali metal salts are suitable, and the sodium, potassium salts, etc. are desirable. Normally, the reaction is desirably conducted in an appropriate solvent, and useful solvents are, for example, water, alcohols such as methanol, ethanol, n-propanol, isopropanol, n-butanol and t-butanol, aromatic hydrocarbons such as benzene, toluene and xylene, halogenated hydrocarbons such as methylene chloride, chloroform and carbon tetrachloride, ethers such as ethyl ether, dioxane and tetrahydrofurane, ketones such as acetone and methyl ethyl ketone, nitriles such as acetonitrile, etc., acid amides such as dimethylformamide, etc., esters such as ethyl acetate, etc., and sulfoxides such as dimethylsulfoxide, etc.

As to the reaction temperature, the temperature at which the reaction may proceed can be suitably selected from the range of $-20°$ C. to $150°$ C., and the temperature of $0°$ C. to $100°$ C. is suitable. The reaction goes to completion within 0.5 to 10 hours, whereby the conclusion of the reaction may be confirmed by thin-layer chromatography, etc.

After the conclusion of the reaction, the resultant reaction mixture is subjected to a procedure conventional per se to obtain the desired compound. For example, the reaction solution is directly washed with water or freed of the solvent, and then extracted with an organic solvent such as toluene, etc., followed by washing with water, drying over, e.g., anhydrous sodium sulfate, and distilling off the solvent to obtain the compound of the present invention. If desired, the compound may be further purified by such procedures as distillation, recrystallization and column chromatography.

Moreover, the compound (I) according to the present invention may be produced by esterifying a compound of the general formula (II) or its salt with a compound designated by the general formula (IV):

(IV)

wherein $R^2$, X and Hal are as defined hereinbefore, in the same manner as the reaction of a compound (II) with one of (III) as described hereinbefore, to obtain a compound represented by the general formula (V):

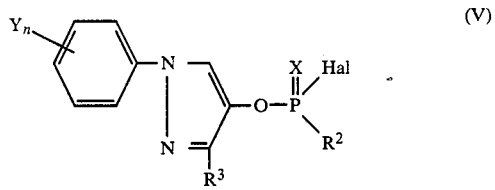

(V)

wherein $R^2$, $R^3$, X, Y, Hal, and n are as defined hereinbefore, followed by reacting the esterified compound with a compound designated by the formula $R^1OH$ whose $R^1$ is as defined hereinbefore, under the same conditions as those of the reaction of compound (II) with compound (III) provided that water and alcohols are not suitable as the solvent.

In addition, among the compounds of the general formula (I), a compound designated by the general formula (VI)

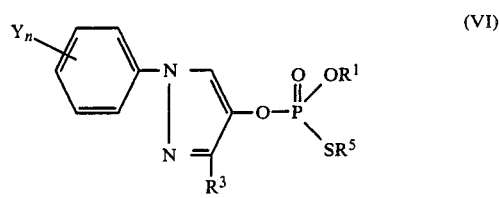

(VI)

wherein $R^1$, $R^3$, Y and n have the same meaning as above, and $R^5$ means a lower alkyl group, may be produced by reacting a metal or ammonium salt of O-lower-alkyl-O-(1-phenylpyrazol-4-yl)phosphorothioic acid designated by the general formula (VII):

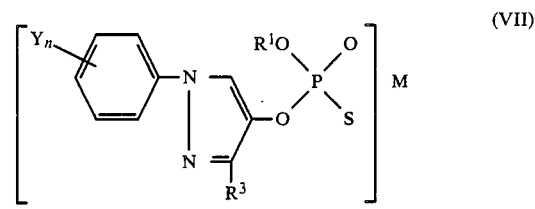

(VII)

wherein $R^1$, $R^3$, Y and n are as defined hereinbefore and M is a metal atom or ammonium radical, with an alkylating agent, as conventionally utilized, represented by the general formula (VIII):

(VIII)

wherein Hal represents a halogen atom; $R^5$ is as defined hereinbefore and φ means phenyl group.

The lower alkyl group designated by $R^5$ is exemplified by methyl, ethyl, n-propyl, isopropyl, n-butyl, isobutyl, sec-butyl groups, etc.

The reaction may be conducted under the conditions similar to those in the reaction of a compound of the general formula (II) with one of (III) as described hereinbefore, and, in the case of a branched, lower alkyl halide being utilized, the reaction may be favorably carried out by prolonging the reaction time slightly. A starting compound of the general formula (VII) is produced by the normally utilized, known methods; namely, by the procedure of reacting O-lower alkyl-O-(1-phenylpyrazol-4-yl)phosphorochloridothionate, the compounds represented by the general formula (V) wherein X is sulfur atom, $R^2$ is a lower alkoxy group and Hal is chlorine atom, with alkali metal, or of reacting O,O-di-lower alkyl-O-(1-phenylpyrazol-4-yl)phosphorothionate, the compounds represented by the general formula (I) wherein X is sulfur atom and $R^2$ is a lower alkoxy group, in anhydrous alcohol, with sodium hydrogen sulfide, sodium alkyl mercaptide, sodium xanthate or potassium xanthate, etc.

The starting compound of the general formula (II) which is used in these reactions may be produced by the procedure as shown in the following equation and described in Annalen der Chemie, 313 12 (1900) or procedures similar thereto:

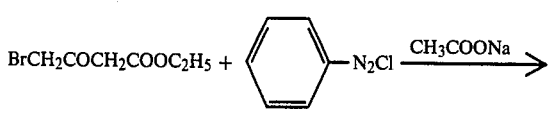

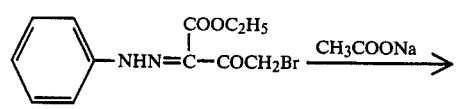

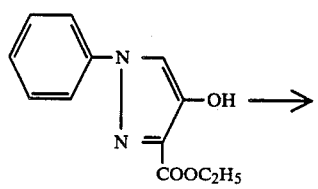

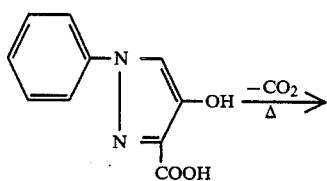

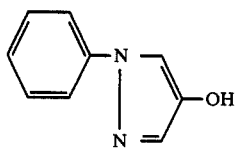

In addition, the present inventors carried out research work on a novel process for producing the starting compound of the general formula (II) (wherein $R^3=H$) which is industrially advantageous, and found out the route described below that can provide a compound of the general formula (II) (wherein $R^3=H$) under mild conditions and in increased yield. In other words, the method according to the present invention is highly valuable as an industrial production process, and many of the starting compounds of the general formula (II) (wherein $R^3=H$) according to the present invention may be produced in accordance with the method.

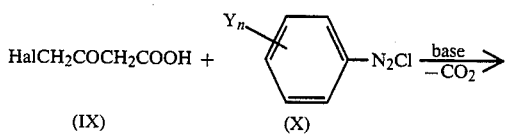

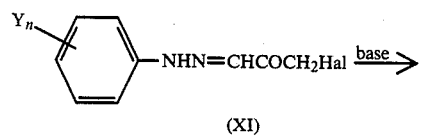

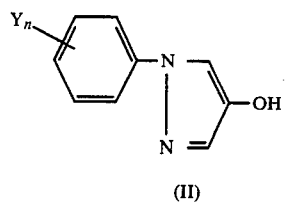

(II)

The method comprises allowing diazonium salts designated by the general formula (X) to act on 4-haloacetoacetic acid represented by the general formula (IX) in the presence of a base to produce 3-halopyruvaldehyde phenylhydrazones designated by the general formula (XI) and subjecting the obtained compound to ring closure reaction in the presence of a base to produce the compounds of the general formula (II) (wherein $R^3=H$).

The reaction that provides 3-halopyruvaldehyde phenylhydrazones represented by the general formula (XI) is normally conducted at a temperature of $-10°$ C. to 30° C. Water is suitable as the solvent but, so as to prevent the resultant crystals from being burst by carbon dioxide gas evolved, alcohols such as methanol, ethanol and propanol may be added. Utilizable as the base are organic carboxylic acid salts, carbonates, hydrogencarbonates, hydroxides, etc. of alkali and alkaline earth metals such as sodium acetate, potassium acetate, sodium propionate, potassium propionate, sodium carbonate, potassium carbonate, sodium hydrogen carbonate, potassium hydrogen carbonate, sodium hydroxide and potassium hydroxide.

Then, the reaction that affords a compound of the general formula (II) (wherein $R^3=H$) from a compound of the general formula (XI) is conducted in the presence of a base. Useful as the base are hydroxides, carbonates and hydrogen carbonates of alkali and alkaline earth metals as well as alcoholates of alkali metals such as sodium carbonate, potassium carbonate, sodium hydrogen carbonate, potassium hydrogen carbonate, sodium methylate and sodium ethylate, and desirable, among others, are strongly basic ones such as sodium hydroxide, potassium hydroxide and alcoholates of alkali metals. The amount of a base that is useful in the reaction, from an economical point of view, is suitably employed in the proportion of 1 to 3 moles to 1 mole of the compound of (XI), although the use of a large excess may be justifiable. The reaction is preferably carried out in a solvent, and utilizable as the solvent are, for example, water; alcohols such as methanol, ethanol, n-propanol, iso-propanol, n-butanol, and t-butanol; ethers such as ethyl ether, dioxane and tetrahydrofuran; ketones such as acetone and methyl ethyl ketone; nitriles such as acetonitrile, etc.; acid amides such as dimethylformamide, etc.; and sulfoxides such as dimethyl sulfoxide, etc. The reaction usually proceeds at a temperature within the range of from $-20°$ C. to 100° C., and proceeds easily even at a temperature of not higher than 0° C. in alcohols, when sodium hydroxide, potassium hydroxide, alcoholate of alkali metals, or the like is employed as a base.

The present method, even when the reaction is conducted continuously without isolating the compound (XI) in the course of the reaction process, can afford the desired compound (II) (wherein $R^3=H$) in a high yield.

Illustrated in the following are the examples of synthesis of the starting compound in accordance with the production process as described hereinbefore.

REFERENCE EXAMPLE A

Synthesis of 1-(4-chlorophenyl)-4-hydroxypyrazole (Compound No.e)

In 50 ml of methanol is dissolved 4.0 g of sodium hydroxide and, when 9.3 g of 3-chloropyruvaledehyde 4-chlorophenylhydrazone is added to the solution at room temperature, it dissolves immediately and the temperature of the solution rises to about 40° C. After being stirred for 1 hour, methanol is distilled off, and 50 ml of water is added to the resultant residue to remove insolubles by filtration. Following neutralization with concentrated hydrochloric acid, the precipitate is recovered by filtration, washed with water and dried. Recrystallization from toluene yields 6.4 g of the subject compound as needle-like crystals. m.p. 127° C. to 128° C.

REFERENCE EXAMPLE B

Synthesis of 1-(4-chlorophenyl)-4-hydroxypyrazole (Compound No.e)

4.0 g of sodium hydroxide is dissolved in 50 ml of water, in which is suspended 9.3 g of 3-chloropyruvaldehyde 4-chlorophenylhydrazone. The suspension is stirred at 50° C. for 3 hours. The crystals dissolve gradually, and the suspension becomes a homogeneous dark-red solution. The solution is cooled and the insolubles are removed by filtration, then the remaining solution is neutralized with concentrated hydrochloric acid. The resulting precipitates are collected by filtration, washed with water and dried. Recrystallization from toluene yields 5.7 g of the subject compound. m.p. 127° to 128° C.

REFERENCE EXAMPLE C

Synthesis of 1-(2,4-dichlorophenyl)-4-hydroxypyrazole (Compound No. n)

27.0 g of 3-chloropyruvaldehyde 2,4-dichlorophenylhydrazone is suspended in 100 ml of ethanol. To the suspension is added at room temperature 12 g of sodium hydroxide dissolved in 10 ml of water. After stirring the mixture for 2 hours ethanol is distilled off, and water is added to the resultant residue to dissolve it. Insolubles are removed by filtration, and the filtrate is neutralized with glacial acetic acid. The precipitate is recovered by filtration, washed with water and dried. Recrystallization from toluene results in 17.3 g of the subject compound in the yield of 87%.

m.p. 148° to 149° C.

Illustrated in the following Table are the compounds of the general formula (II) (R³=H) as synthesized according to the procedures of Reference Examples A through C.

TABLE

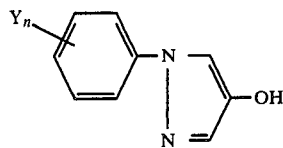
(II)

| No. | $Y_n$ | n | melting point, °C. |
|---|---|---|---|
| a | — | 0 | 118–120 |
| b | 4-Br | 1 | 157–159 |
| c | 2-Cl | 1 | 105–106 |
| d | 3-Cl | 1 | 98–99 |
| e | 4-Cl | 1 | 127–128 |
| f | 4-F | 1 | 155–157 |
| g | 4-I | 1 | 203–205 |
| h | 2-CH$_3$ | 1 | 128–130 |
| i | 4-CH$_3$ | 1 | 125–127 |
| j | 4-n-C$_3$H$_7$ | 1 | 101–102 |
| k | 4-CH$_3$O | 1 | 111–112 |
| l | 4-CH$_3$S | 1 | 127 |
| m | 3-CF$_3$ | 1 | 96–97 |
| n | 2,4-Cl$_2$ | 2 | 148–149 |
| o | 3,4-Cl$_2$ | 2 | 152–154 |
| p | 3,5-Cl$_2$ | 2 | 125–127 |
| q | 2,4-(CH$_3$)$_2$ | 2 | 122–124 |
| r | 2,6-(CH$_3$)$_2$ | 2 | 169–170 |
| s | 2-F, 4-Cl | 2 | 137–139 |
| t | 2-CH$_3$, 4-Cl | 2 | 102–104 |
| u | 2-CH$_3$, 5-NO$_2$ | 2 | 128–130 |
| v | 3,4-CH$_2$$\begin{smallmatrix}O-\\O-\end{smallmatrix}$ | 2 | 125–126 |
| w | 2,4,5-Cl$_3$ | 3 | 181–183 |

REFERENCE EXAMPLE D

Synthesis of 3-chloropyruvaldehyde 4-chlorophenylhydrazone (Compound No. f')

In a mixture of 500 ml of water and 250 ml of concentrated hydrochloric acid is dissolved 128 g of p-chloroaniline. To this solution is added dropwise a solution of 69 g of sodium nitrite in 100 ml of water, while the reaction temperature is maintained at 0° C. Then, to the reaction mixture is added a solution of 136.5 g of 4-chloroacetoacetic acid in 200 ml of water, while the reaction temperature is maintained within the range from 0° C. to 5° C., followed by further addition of a solution of 164 g of sodium acetate in 300 ml of water, whereupon yellow precipitate is produced while bubbling vigorously. The reaction mixture is stirred at a room temperature until the bubbling ceases, followed by collecting the crystals by filtration, washing with water and drying, whereby 224 g of the subject compound is obtained.

Yield 97%.

m.p. 190° C.–192° C. (decomp.)

Illustrated in the following Table are the starting compounds of the general formula (XI) synthesized by the same procedure as described in Reference Example D.

TABLE

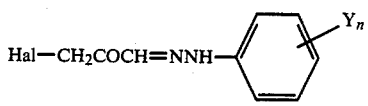

Hal—CH₂COCH=NNH—[phenyl ring with Y$_n$]

| No. | Hal | Y$_n$ | n | melting point, °C.* |
|---|---|---|---|---|
| a' | Br | — | 0 | 178–180 |
| b' | " | 4-Br | 1 | 182–184 |
| c' | " | 2-Cl | 1 | 97–99 |
| d' | " | 3-Cl | 1 | 152–154 |
| e' | " | 4-Cl | 1 | 175–177 |
| f' | Cl | 4-Cl | 1 | 190–192 |
| g' | Br | 4-F | 1 | 178–180 |
| h' | " | 4-I | 1 | 170–172 |
| i' | " | 2-CH$_3$ | 1 | 105–108 |
| j' | " | 4-CH$_3$ | 1 | 158–160 |
| k' | " | 4-n-C$_3$H$_7$ | 1 | 120–121 |
| l' | " | 4-CH$_3$O | 1 | 138–140 |
| m' | " | 3-CF$_3$ | 1 | 121–123 |
| n' | " | 2,4-Cl$_2$ | 2 | 132–134 |
| o' | " | 3,4-Cl$_2$ | 2 | 168–170 |
| p' | " | 3,5-Cl$_2$ | 2 | 181–183 |
| q' | " | 2,4-(CH$_3$)$_2$ | 2 | 125–127 |
| r' | " | 2,6-(CH$_3$)$_2$ | 2 | 98–99 |
| s' | " | 2-F, 4-Cl | 2 | 133–135 |
| t' | " | 2-CH$_3$, 4-Cl | 2 | 158–160 |
| u' | " | 2-CH$_3$, 5-NO$_2$ | 2 | 170–173 |
| v' | " | 3,4-CH$_2$⟨O—/O—⟩ | 2 | 136–137 |
| w' | " | 2,4,5-Cl$_3$ | 3 | 153–155 |

Remarks:
Melting points indicated are all the decomposition temperature.

The phosphorochloridates represented by the general formula (III) or (IV) may be easily produced by the procedures already known or similar thereto.

The compounds of (I) according to the present invention are effective for controlling unsanitary pests, insects parasitic on plants, and mites.

In more particular, the compounds according to the present invention and preparations containing the same are effective especially for prevention and extermination of injurious insects of the order Hemiptera such as *Eurydema rugosa, Scotinophara laurida, Riptortus clavatus, Stephanitis nashi, Laodelphax stiatellus, Nephotettix cincticeps, Unaspis yanonensis, Aphis glycines, Lipaphis pseudobrassicae, Brevicoryne brassicae,* and *Aphis gossypii;* injurious insects of the order Lepidoptera such as *Spodoptera litura, Plutella xylostella, Pieris rape crucivora, Chilo suppressalis, Plusia nigrisigna, Halicoverpa assulta, Leucania separate, Mamestra brassicae, Adoxophyes orana, Syllepte derogate, Cnaphalocrocis medinalis, Phthorimaea operculella,* etc.; injurious insects of the order Coleoptera such as *Epilachna vigintioctopunctata, Aulacophora femoralis, Phyllotreta striolata, Oulema orgzae* and *Echinocnemus squameus;* injurious insects of the order Diptera such as *Musca domestica, Culex pipiens pallens, Tabanus trigonus, Hylemya antiqua* and *Hylemya platura;* injurious insects of the order Orthoptera such as *Locusta migratoria, Gryllotalpa africana,* etc.; injurious insects of the order Blattaria such as *Blattella germanica, Periplaneta fuliginosa,* etc.; spider mites (the order Tetranychidae) such as *Tetranychus urticae, Panonychus citri, Tetranychus kanzawai, Tetranychus cinnabarinus, Panonychus ulmi* and eriophyid mites (Eriophyidae) such as *Aculus pelekassi;* ticks such as Ixodidae; such nematodes as *Aphelenchoides besseyi,* and the like.

For use as an insecticidal-acaricidal agent, the compound (I) according to this invention may take any of the known application formulations of agricultural chemicals. Thus, for example, one or more species of compound (I) are dissolved or dispersed in a suitable liquid carrier or admixed with, or adsorbed on, a suitable solid carrier to prepare an emulsifiable concentrate, oil solution, wettable powder, dust, granule, tablet, spray, paint, ointment or the like. If necessary, emulsifiers, suspension aids, spreading agents, penetrating agents, wetting agents, thickeners, stabilizers, etc. may also be incorporated in such compositions. These preparations can be produced by known manufacturing methods.

The content of the active component in insecticidal-miticidal preparations, although it varies depending upon their application purposes, is suitably about 10 to 90 percent by weight for the emulsifiable concentrates, wettable powder, etc., 0.1 to 10 percent by weight in the oil preparations, powder or dusts, etc., and 1 to 20 percent by weight for the granules. Furthermore, these concentrations may be properly changed with the application purposes, while the emulsifiable concentrates, wettable powder and the like, prior to their application, may be advantageously diluted and extended (up to 100 to 100000 times, for example) appropriately with water, etc. to be dispersed therein.

Suitable as the liquid carriers to be employed are, for example, water, alcohols (e.g., methyl alcohol, ethyl alcohol, ethylene glycol, etc.), ketones (e.g., acetone, methyl ethyl ketone, etc.), ethers (e.g., dioxane, tetrahydrofurane, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.), halogenated hydrocarbons (e.g., chloroform, carbon tetrachloride, etc.), acid amides (e.g., dimethylformamide), esters (e.g., ethyl acetate, butyl acetate, glycerol esters of fatty acids, etc.), nitriles (e.g., acetonitrile), and other solvents, and one kind or a mixture of not less than two kinds of these is used.

Examples of useful solid carriers include powder of plant origin (e.g., soybean meal, tobacco powder, wheat flour, wood flour, etc.), powder of mineral origin (e.g., clay such as kaolin, bentonite and acid clay, talc such as talcum powder and pegotite powder, silica such as diatomaceous earth and mica powder, and the like), alumina, sulfur powder, activated carbon, etc., and one kind or a mixture of not less than two kinds of these is employed.

The ointment excipients are exemplified by polyethylene glycol, pectin, polyhydric alcohol esters of higher fatty acids such as glycerol monostearate, cellulose derivatives such as methylcellulose, sodium arginate, bentonite, higher alcohols, polyhydric alcohols such as glycerol, petrolatum, white petrolatum, liquid paraffin, lard, a variety of oils of plant origin, lanolin, lanolin anhydricum, hardened oil, resins, and the like, out of which one or not less than two kinds, directly or added with various surfactants, can be properly selected.

Among the surfactants which are useful as emulsifiers, spreaders, penetrants, dispersing agents, etc., employable as occasion demands are soaps, polyoxyaryl esters (e.g., Nonal ® produced by Takemoto Oils & Fats Co., Ltd.), alkyl sulfates (e.g., Emal 10 ®, Emal 40 ®, etc. produced by Kao Atlas Co., Ltd.), alkyl sulfonates (e.g., Neogen ® Neogen TR ®, etc. produced by Daiichi Kogyo Seiyaku Co., Ltd.; Neoperex ® produced by Kao Atlas Co., Ltd.), polyethylene glycol ethers (e.g., Nonipol 85 ®, Nonipol 100 ®, and Nonipol 160 ® produced by Sanyo Chemical Industries Co., Ltd.), polyhydric alcohol esters (e.g., Tween 20 ® and Tween 80 ® produced by Kao Atlas Co., Ltd.), and the like. In addition, the compounds of the present invention may be used in mixture by formulating them with, for example, other kinds of insecticides (pyrethrin-based insecticides, organic phosphorus insecticides, carbamate insecticides, naturally occurring insecticides, etc.), acaricides, nematocides, herbicides, plant hormone preparations, plant growth control substances, fungicides and bactericides (e.g. copper based fungicides, organic cholorinated fungicides, organo-sulfur fungicides, phenol based fungicides, etc.), synergists, attractants, repellents, coloring matters, fertilizers, etc.

The composition containing the compound (I) can be employed to control the above-mentioned insects, mites or ticks attacking for example, dry field harvest, such as cabbages, soy beans, maize, cotton, and tobacco; fruit trees of apples, oranges, etc. The composition can also be applied fo cattle directly or the inside and outside of cattle barns or poultry houses. The amount of the effective component to be used is usually within the range of from ca. 50 g to ca. 5 kg per ha., preferably from ca. 100 g to ca. 3 kg per ha.

The following examples serve to illustrate the present invention but should not be construed as imposing any limitations on the present invention.

EXAMPLE 1

Production of
O-ethyl-O-(1-phenylpyrazol-4-yl)-S-n-propylphosphorothiolate (Compound No. 4)

In 50 ml of methanol is dissolved 0.5 g of metallic sodium, and 3.2 g of 1-phenyl-4-hydroxypyrazole is added thereto. Complete removal of methanol under reduced pressure gives sodium salt of 1-phenyl-4-hydroxypyrazole. The sodium salt is suspended in 60 ml of methyl ethyl ketone, and 4.0 g of O-ethyl-S-n-propylphosphorochloridothiolate is added to the suspension, followed by stirring at room temperature for 3 hours. After the conclusion of the reaction, methyl ethyl ketone is ditilled off, and toluene is added to the residue. The toluene layer is washed with water, and dried over anhydrous sodium sulfate. After distilling off toluene, the residue is purified by silica-gel column chromatography (developing solvent; chloroform). In this way, there is obtained 4.9 g of the subject compound in slightly yellow, oily form. $n_I^{28}$ 1.5407.

EXAMPLE 2

Production of
O-ethyl-O-(1-phenylpyrazol-4-yl)-S-n-propyl phosphorothiolothionate (Compound No. 5)

In 60 ml of acetone is suspended 3.6 g (0.02 mol) of sodium salt of 1-phenyl-4-hydroxypyrazole, and 4.4 g of O-ethyl-S-n-propyl phosphorochloridothiolothionate is added to the suspension. The mixture is heated under reflux for 3 hours, followed by removal of acetone by evaporation. To the residue is added toluene. The toluene layer is washed with water and dried over anhydrous sodium sulfate. Toluene is distilled off, and the residue is purified by silica-gel column chromatography (developing solvent: chloroform). By the above procedure, there is obtained 4.7 g of slightly yellow and oily compound as captioned above. $n_D^{30}$ 1.5783.

EXAMPLE 3

Production of
O-ethyl-O-[1-(4-chlorophenyl)pyrazol-4-yl]-S-n-propyl phosphorothiolate (Compound No. 16)

In 60 ml of acetonitrile is dissolved 3.9 g of 1-(4-chlorophenyl)-4-hydroxypyrazole, and 2.0 g of triethylamine is added thereto. Then, 4.0 g of O-ethyl-S-n-propyl phosphorochloridothiolate, followed by stirring at 50° C. for 3 hours. Acetonitrile is then distilled off and purification is conducted in accordance with the procedure of Example 1, yields 5.2 g of slightly yellow and oily compound as captioned above. $n_D^{24}$ 1.5604.

EXAMPLE 4

Production of
O-ethyl-O-[1-(3,4-dichlorophenyl)pyrazol-4-yl]-S-n-propyl phosphorothiolate (Compound No. 31)

In 60 ml of methyl ethyl ketone is dissolved 4.6 g of 1-(3,4-dichlorophenyl)-4-hydroxypyrazole, and 2.8 g of potassium carbonate and 4.0 g of O-ethyl-S-n-propyl phosphorochloridothiolate, followed by stirring at 50° C. for 2 hours. Purification carried out in accordance with the procedure of Example 1 yields 5.9 g of the slightly yellow and oily compound as captioned above. $n_D^{27}$ 1.5737.

EXAMPLE 5

Production of
O-ethyl-O-[1-(4-chlorophenyl)pyrazol-4-yl]-S-n-propyl phosphorothiolate (Compound No. 16)

To 60 ml of ethanol are added 6.8 g of sodium O-ethyl-O-[1-(4-chlorophenyl)pyrazol-4-yl]phosphorothiolate and 2.7 g of n-propyl bromide, followed by stirring at 70° C. for 8 hours. The resultant inorganic salt is filtered off, ethanol being removed, and to the residue is added toluene. The toluene layer is washed with water and dried. Purification carried out in accordance with the procedure of Example 1 yields 5.0 g of slightly yellow and oily compound as captioned above. $n_D^{24}$ 1.5604.

Shown in the following Table 1 are compounds produced in the same manner as in Examples 1 to 5, inclusive of those obtained in Examples 1 to 5.

TABLE 1

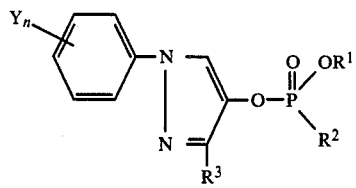

| Comp. No. | R¹ | R² | R³ | X | Yₙ | n | Physical constant |
|---|---|---|---|---|---|---|---|
| 1 | CH₃ | OCH₃ | H | S | — | 0 | $n_D^{28}$ 1.5696 |
| 2 | C₂H₅ | OC₂H₅ | H | S | — | 0 | $n_D^{26}$ 1.5520 |
| 3 | C₂H₅ | OC₃H₇(n) | H | S | — | 0 | $n_D^{28}$ 1.5425 |
| 4 | C₂H₅ | SC₃H₇(n) | H | O | — | 0 | $n_D^{28}$ 1.5407 |
| 5 | C₂H₅ | SC₃H₇(n) | H | S | — | 0 | $n_D^{30}$ 1.5783 |
| 6 | C₂H₅ | OC₃H₇(n) | —COOC₂H₅ | S | — | 0 | $n_D^{26}$ 1.5432 |
| 7 | C₂H₅ | SC₃H₇(n) | —COOC₂H₅ | O | — | 0 | $n_D^{20}$ 1.5434 |
| 8 | C₂H₅ | SC₃H₇(n) | —COOC₂H₅ | S | — | 0 | $n_D^{20}$ 1.5683 |
| 9 | C₂H₅ | SC₃H₇(n) | H | O | 4-Br | 1 | $n_D^{20}$ 1.5755 |
| 10 | C₂H₅ | SC₃H₇(n) | H | S | 4-Br | 1 | $n_D^{27}$ 1.6025 |
| 11 | C₂H₅ | OC₂H₅ | H | S | 2-Cl | 1 | $n_D^{24}$ 1.5516 |
| 12 | C₂H₅ | SC₃H₇(n) | H | O | 2-Cl | 1 | $n_D^{24}$ 1.5493 |
| 13 | C₂H₅ | SC₃H₇(n) | H | O | 3-Cl | 1 | $n_D^{20}$ 1.5655 |
| 14 | C₂H₅ | SC₃H₇(n) | H | S | 3-Cl | 1 | $n_D^{24}$ 1.5922 |
| 15 | C₂H₅ | OC₂H₅ | H | S | 4-Cl | 1 | $n_D^{24}$ 1.5635 |
| 16 | C₂H₅ | SC₃H₇(n) | H | O | 4-Cl | 1 | $n_D^{24}$ 1.5604 |
| 17 | C₂H₅ | SC₃H₇(n) | H | S | 4-Cl | 1 | $n_D^{20}$ 1.5933 |
| 18 | C₂H₅ | SC₃H₇(n) | H | O | 4-F | 1 | $n_D^{20}$ 1.5368 |
| 19 | C₂H₅ | SC₃H₇(n) | H | S | 4-F | 1 | $n_D^{28}$ 1.5695 |
| 20 | C₂H₅ | SC₃H₇(n) | H | O | 4-I | 1 | $n_D^{20}$ 1.6000 |
| 21 | C₂H₅ | OC₂H₅ | H | S | 2-CH₃ | 1 | $n_D^{24}$ 1.5517 |
| 22 | C₂H₅ | SC₃H₇(n) | H | O | 2-CH₃ | 1 | $n_D^{25}$ 1.5525 |
| 23 | C₂H₅ | SC₃H₇(n) | H | O | 4-CH₃ | 1 | $n_D^{25}$ 1.5409 |
| 24 | C₂H₅ | SC₃H₇(n) | H | O | 4-C₃H₇(n) | 1 | $n_D^{20}$ 1.5446 |
| 25 | C₂H₅ | SC₃H₇(n) | H | S | 4-CH₃O | 1 | $n_D^{28}$ 1.5757 |
| 26 | C₂H₅ | SC₃H₇(n) | H | O | 4-CH₃S | 1 | $n_D^{20}$ 1.5883 |
| 27 | C₂H₅ | SC₃H₇(n) | H | O | 3-CF₃ | 1 | $n_D^{20}$ 1.5169 |
| 28 | C₂H₅ | SC₃H₇(n) | H | S | 3-CF₃ | 1 | $n_D^{20}$ 1.5445 |
| 29 | C₂H₅ | SC₃H₇(n) | H | O | 2,4-Cl₂ | 2 | $n_D^{27}$ 1.5586 |
| 30 | C₂H₅ | SC₃H₇(n) | H | S | 2,4-Cl₂ | 2 | $n_D^{20}$ 1.5893 |
| 31 | C₂H₅ | SC₃H₇(n) | H | O | 3,4-Cl₂ | 2 | $n_D^{27}$ 1.5737 |
| 32 | C₂H₅ | SC₃H₇(n) | H | S | 3,4-Cl₂ | 2 | $n_D^{20}$ 1.5982 |
| 33 | C₂H₅ | SC₃H₇(n) | H | O | 3,5-Cl₂ | 2 | $n_D^{26}$ 1.5698 |
| 34 | C₂H₅ | OC₂H₅ | H | S | 2,4-(CH₃)₂ | 2 | $n_D^{27}$ 1.5361 |
| 35 | C₂H₅ | SC₃H₇(n) | H | O | 2,4-(CH₃)₂ | 2 | $n_D^{27}$ 1.5355 |
| 36 | C₂H₅ | SC₃H₇(n) | H | O | 2,6-(CH₃)₂ | 2 | $n_D^{28}$ 1.5264 |
| 37 | C₂H₅ | SC₃H₇(n) | H | O | 2-F,4-Cl | 2 | $n_D^{28}$ 1.5481 |
| 38 | C₂H₅ | SC₃H₇(n) | H | O | 2-CH₃,4-Cl | 2 | $n_D^{28}$ 1.5474 |
| 39 | C₂H₅ | SC₃H₇(n) | H | O | 2-CH₃,5-NO₂ | 2 | $n_D^{20}$ 1.5566 |
| 40 | C₂H₅ | SC₃H₇(n) | H | S | 2-CH₃,5-NO₂ | 2 | $n_D^{20}$ 1.5822 |
| 41 | C₂H₅ | SC₃H₇(n) | H | O | 3,4-CH₂(O—)₂ | 2 | $n_D^{28}$ 1.5481 |
| 42 | C₂H₅ | SC₃H₇(n) | H | O | 2,4,5-Cl₃ | 3 | $n_D^{28}$ 1.5722 |
| 43 | C₂H₅ | SC₃H₇(n) | H | S | 2,4,5-Cl₃ | 3 | $n_D^{20}$ 1.5994 |

EXAMPLE 6

| Emulsifiable concentrate | |
|---|---|
| Compound No. 16 | 20 weight % |
| Xylene | 75 weight % |
| Polyoxyethylene glycol ether (Nonipol 85 ®) | 5 weight % |

An emulsifiable concentrate is produced by mixing the above ingredients.

EXAMPLE 7

| Wettable powder | |
|---|---|
| Compound No. 17 | 30 weight % |
| Sodium lignin sulfonate | 5 weight % |
| Polyoxyethylene glycol ether (Nonipol 85 ®) | 5 weight % |
| White carbon | 30 weight % |
| Clay | 30 weight % |

A wettable powder is produced by mixing the above ingredients.

EXAMPLE 8

| Dust | |
|---|---|
| Compound No. 31 | 3 weight % |
| White carbon | 3 weight % |

-continued

| Dust | |
|---|---|
| Clay | 94 weight % |

A dust is produced by mixing the above ingredients.

EXAMPLE 9

| Granules | |
|---|---|
| Compound No. 9 | 10 weight % |
| Sodium lignin sulfonate | 5 weight % |
| Clay | 85 weight % |

Granules are produced by mixing the above ingredients.

EXAMPLE 10

Testing Example 1; Effective against *Laodelphax striatellus*

(a) A test compound was processed into an emulsifiable concentrate in accordance with the formulation of Example 6, followed by diluting with water to prepare a treating solution of a 40 ppm concentrate. 2.5 ml of the treating solution was placed into a test tube (with 1.7 cm of diameter, 4 cm deep), in which three seedlings of a paddyrice plant (on the 7th day after germination) were allowed to stand so their root portions were dipped into the solution for 2 hours. The seedlings were then transferred into a test tube having 1 ml water placed in the bottom, and ten third-instar larvae of *Laodelphax striatellus* were released. After allowing the test tube to stand in the room (28° C.) for 24 hours, the dead larvae were counted. The test is repeated twice, and the test results are tabulated, in terms of mortality, in Table 2 (I).

(b) A test compound was processed into a dust preparation in accordance with the formulation of Example 8, and 500 mg of the preparation was dusted on the potted paddy-rice plant (1/5,000 a) by the Berger Duster method. After dusting, leaves (15 cm long) of the paddy rice were cut off and were placed in a test tube containing 1 ml of water in the bottom, and ten adults of *Laodelphax striatellus* were released therein. After allowing the test tube to stand in the room (28° C.) for 24 hours, the dead insects were counted. The test was repeated twice, and the test results, in terms of mortality, are tabulated in Table 2 (II).

TABLE 2

| Comp. No. | Mortality, % | |
|---|---|---|
| | (I) | (II) |
| 6 | 97 | 70 |
| 9 | 100 | 75 |
| 13 | 100 | 90 |
| 16 | 97 | 75 |
| 17 | 100 | 35 |
| 18 | 100 | 100 |
| 20 | 100 | 65 |
| 22 | 85 | 63 |
| 24 | 85 | 50 |
| 29 | 95 | 30 |
| 31 | 100 | 90 |
| 33 | 100 | 65 |
| 37 | 100 | 90 |
| 42 | 100 | 40 |
| 43 | 85 | 40 |
| Non-treated | 0 | 0 |

Testing Example 2; Effectiveness against *Spodoptera litura*

Twenty milliliters of a 500 ppm, water-diluted solution (with Dyne ®, Takeda Chem. Ind. Ltd., spreading agent, as diluted 3000-fold) of the test compound (the emulsifiable concentrate of Example 6) was sprayed on grown seedlings (10 days after germination) of soybean plant water-cultured in a polyethylene cup by the use of a spray gun (nozzle pressure of 1 kg/cm² gauge) in a spraying chamber. 2 hours after spraying, two main leaves of soybean plant were cut off and were placed into two cups (6 cm in diameter and 4 cm in depth), respectively, and ten second-instar larvae of Spondoptera litura were liberated. The cups were left in the room (28° C.) for 24 hours, and the dead larvae were counted. The test was repeated twice, and the test results in terms of mortality are tabulated in Table 3.

TABLE 3

| Comp. No. | Mortality, % |
|---|---|
| 4 | 100 |
| 5 | 100 |
| 7 | 100 |
| 8 | 100 |
| 9 | 100 |
| 10 | 100 |
| 12 | 100 |
| 13 | 100 |
| 14 | 100 |
| 16 | 100 |
| 17 | 100 |
| 18 | 100 |
| 19 | 100 |
| 20 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| Non-treated | 0 |

Testing Example 3; Effectiveness of *Unaspis yanonensis*

A test compound was processed into a wettable powder in accordance with the formulation of Example 7, and was diluted with water (with Dyne ®, spreading agent, as diluted 3000-fold) to prepare a 500 ppm aqueous suspension. 20 ml of the aqueous suspension was sprayed on second-instar larvae (10 to 50 of the number parasitized) of *Unaspis yanonensis* on a seedling of *Citrus trifoliate* (2 months after germination) being planted in a pot (9 cm in diameter). After the sprayed pot was transferred to a greenhouse (25° to 30° C.), adult insects were counted on the 20th day after spraying. The test was repeated twice, and the test results in terms of mortality are tabulated in Table 4. Mortality (%) is calculated by the following equation:

$$\text{Mortality (\%)} = 100 - \frac{\text{number of grown adults}}{\text{number of 2nd-instar larvae}} \times 100$$

TABLE 4

| Comp. No. | Mortality, % |
|---|---|
| 1 | 86 |
| 2 | 75 |
| 3 | 79 |
| 4 | 84 |
| 12 | 71 |
| 25 | 100 |
| 29 | 97 |
| 31 | 75 |
| 33 | 70 |
| 34 | 79 |
| 35 | 82 |
| Non-treated | 0 |

Testing Example 4; Effectiveness against *Tetranychus urticae*

A test compound was processed into an emulsifiable concentrate in accordance with the formulation of Example 6, and was diluted with water (with Dyne®, spreading agent, as diluted 3000-fold) to prepare a 500 ppm aqueous solution. Ten female adults of Tetranychus urticae were infected on the seedling of a kidney bean plant watercultured in a polyethylene cup, and the cups were placed in a glass chamber (28° C.) for 24 hours, followed by spraying 20 ml of the aqueous solution on the kidney bean plant. After the sprayed cup was placed again in the glass chamber, the number of the adults and larvae living on the leaves was counted on the 2nd and 7th days after spraying. The test was repeated twice, and the test results are tabulated in Table 5 in terms of the efficacy grading as determined by calculating a decrease rate by the following equation:

| Efficacy grading | Decrease rate, % |
|---|---|
| 0 | Not more than 20 |
| 1 | 21 to 50 |
| 2 | 51 to 89 |
| 3 | Not less than 90 |

TABLE 5

| Comp. No. | Efficacy grading 2nd day | 7th day |
|---|---|---|
| 1 | 3 | 3 |
| 3 | 3 | 0 |
| 4 | 3 | 3 |
| 5 | 3 | 3 |
| 7 | 3 | 3 |
| 8 | 3 | 0 |
| 9 | 3 | 3 |
| 10 | 3 | 3 |
| 11 | 3 | 0 |
| 12 | 3 | 3 |
| 13 | 3 | 3 |
| 14 | 3 | 0 |
| 15 | 3 | 0 |
| 16 | 3 | 3 |
| 17 | 3 | 3 |
| 18 | 3 | 3 |
| 19 | 3 | 3 |
| 20 | 3 | 3 |
| 21 | 3 | 0 |
| 22 | 3 | 3 |
| 23 | 3 | 3 |
| 24 | 3 | 3 |
| 25 | 3 | 3 |
| 29 | 3 | 3 |

TABLE 5-continued

| Comp. No. | Efficacy grading 2nd day | 7th day |
|---|---|---|
| 30 | 3 | 3 |
| 31 | 3 | 3 |
| 32 | 3 | 3 |
| 33 | 3 | 3 |
| 35 | 3 | 3 |
| 36 | 3 | 3 |
| 37 | 3 | 3 |
| 38 | 3 | 3 |
| 41 | 3 | 3 |
| 42 | 3 | 3 |
| 43 | 3 | 3 |
| Non-treated | 0 | 0 |

REFERENCE EXAMPLE

Toxicological Test
Below tabulated are the oral acute toxicity values obtained with five-week aged, ddY-SLC strained male mice:

| Comp. No. | $LD_{50}$, mg/kg |
|---|---|
| 1 | >300 |
| 2 | >300 |
| 3 | >300 |
| 4 | >300 |
| 5 | >300 |
| 6 | >300 |
| 7 | >300 |
| 8 | >300 |
| 9 | >300 |
| 10 | >300 |
| 11 | >300 |
| 12 | >300 |
| 13 | >300 |
| 14 | >300 |
| 15 | >300 |
| 16 | >300 |
| 17 | >300 |
| 18 | >300 |
| 19 | >300 |
| 20 | >300 |
| 21 | >300 |
| 22 | ca. 300 |
| 23 | 50 to 300 |
| 24 | >300 |
| 25 | >300 |
| 26 | >300 |
| 27 | 50 to 300 |
| 28 | >300 |
| 29 | ca. 300 |
| 30 | >300 |
| 31 | >300 |
| 32 | >300 |
| 33 | >300 |
| 34 | >300 |
| 35 | ca. 300 |
| 36 | >300 |
| 37 | >300 |
| 38 | >300 |
| 39 | >300 |
| 40 | >300 |
| 41 | 50 to 300 |
| 42 | >300 |
| 43 | >300 |

What is claimed is:

1. A compound selected from the group consisting of 1-[4-halogenophenyl]-4-hydroxypyrazole, 1-(3-,4- or 3,5-dichlorophenyl)-4-hydroxypyrazole, 1-[4-chloro-2-fluorophenyl]-4-hydroxypyrazole, 1-[3-trifluoromethylphenyl]-4-hydroxypyrazole, and a salt thereof.

2. The compound as claimed in claim 1, namely 1-(4-chlorophenyl)-4-hydroxypyrazole or a salt thereof.

3. The compound as claimed in claim 1, namely 1-(3,4-dichlorophenyl)-4-hydroxypyrazole or a salt thereof.

4. The compound as claimed in claim 1, namely 1-(4-fluorophenyl)-4-hydroxypyrazole or a salt thereof.

5. A compound as claimed in claim 1, which is 1-(4-halogenophenyl)-4-hydroxypyrazole or a salt thereof.

* * * * *

Disclaimer 4,621,144.—*Yoshiyuki Okada*, Suita; *Yasuo Sato*, Kyoto, both of Japan. 1-PHENYL-4-HYDROXYPYRAZOLE DERIVATIVES. Patent dated Nov. 4, 1986. Disclaimer filed July 6, 1989, by the assignee, Takeda Chemical Industries, Ltd.

Hereby enters this disclaimer to claims 1, 2 and 5 of said patent.
[*Official Gazette January 16, 1990*]